US00PP17010P2

(12) United States Plant Patent
Pellett

(10) Patent No.: US PP17,010 P2
(45) Date of Patent: Aug. 15, 2006

(54) ***CLEMATIS* PLANT NAMED 'CENTER STAR'**

(50) Latin Name: *Clematis* hybrid
Varietal Denomination: Center Star

(76) Inventor: Harold M. Pellett, 1450 Game Farm Rd., Mound, MN (US) 55364

( * ) Notice: Subject to any disclaimer, the term of this patent is extended or adjusted under 35 U.S.C. 154(b) by 26 days.

(21) Appl. No.: 11/130,672

(22) Filed: May 17, 2005

(51) Int. Cl.
*A01H 5/00* (2006.01)

(52) U.S. Cl. ..... Plt./228

(58) Field of Classification Search ..... Plt./228
See application file for complete search history.

*Primary Examiner*—Kent Bell
*Assistant Examiner*—Annette H Para
(74) *Attorney, Agent, or Firm*—Penny J. Aguirre

(57) ABSTRACT

A new cultivar of hybrid *Clematis,* 'Center Star', characterized by its free-flowering, sterile upward facing blue flowers with showy white centers produced on plants with an upright to decumbent, non-vining habit that exhibit cold hardiness to USDA Zone 3.

2 Drawing Sheets

Botanical classification: *Clematis* hybrid.
Variety denomination: 'Center Star'.

BACKGROUND OF THE INVENTION

The present invention relates to a new and distinct cultivar of *Clematis,* botanically an interspecific hybrid, and will be referred to hereafter by its cultivar name, 'Center Star'. 'Center Star' is grown as an herbaceous perennial for landscape use.

'Center Star' was derived from a formal breeding program conducted by the breeder in Mound, Minn. with a goal of developing non-vining forms of cold hardy *Clematis* with showy flowers. The present invention originated from a controlled cross made in the summer of 2000 between an unnamed selection of *Clematis integrifolia* (female parent) and an unnamed selection of *Clematis hexapetala* (male parent). 'Center Star' was selected in the summer of 2002 and recognized as unique for its upright facing blue colored flowers combined with the non-vining plant habit derived from both parents. The new cultivar differs primarily from the female parent, *Clematis integrifolia,* in having upright facing flowers as opposed to nodding flowers and is unique from the male parent, *Clematis hexapetala,* in having blue flowers rather than white flowers as typical for the species.

Asexual reproduction of the new cultivar was first accomplished by terminal stem cuttings at the University of Minnesota Horticultural Research Center in Chaska, Minn. in summer of 2002 by the inventor. The characteristics of this cultivar have been determined to be stable and are reproduced true to type in successive generations.

SUMMARY OF THE INVENTION

The following traits have been repeatedly observed and represent the characteristics of the new cultivar as grown outdoors in a test plot for three years in Mound, Minn. These attributes in combination distinguish 'Center Star' from other varieties of *Clematis* known to the inventor.

1. Upright facing blue flowers with showy centers comprised of numerous stamen white in color.

2. Free flowering with strong bloom for 4 weeks beginning in mid to late June and scattered bloom throughout the remainder of the growing season in Minnesota.
3. Exhibits an upright to decumbent habit, non-clinging and non-vining.
4. Sterile, no seed heads are produced.
5. Cold hardy to USDA Zone 3.

BRIEF DESCRIPTION OF THE DRAWING

The accompanying colored photographs illustrate the overall appearance and distinct characteristics of the new *Clematis.*

The photograph in FIG. 1 shows the plant and blooming habit and foliage in early July, the plant is bound in twine to remain upright.

Figure 1:
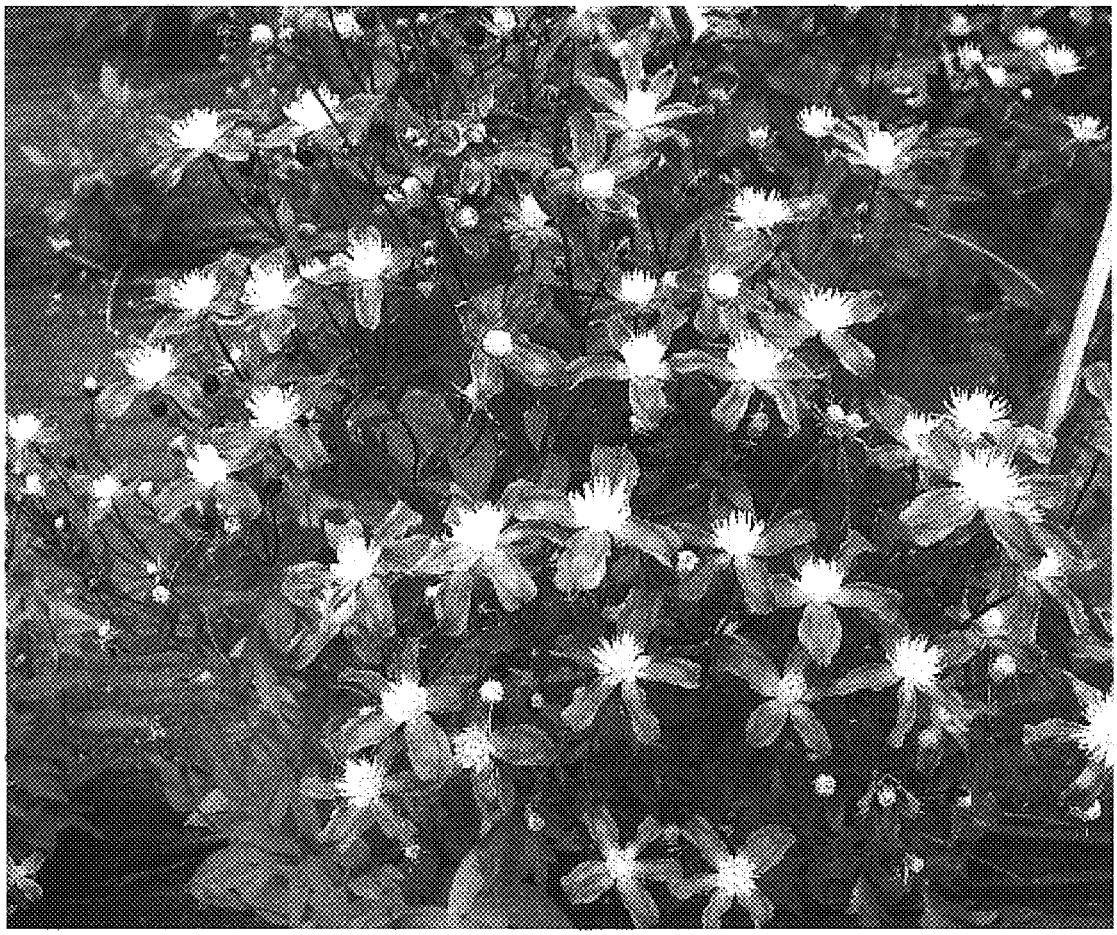
Figure 2:
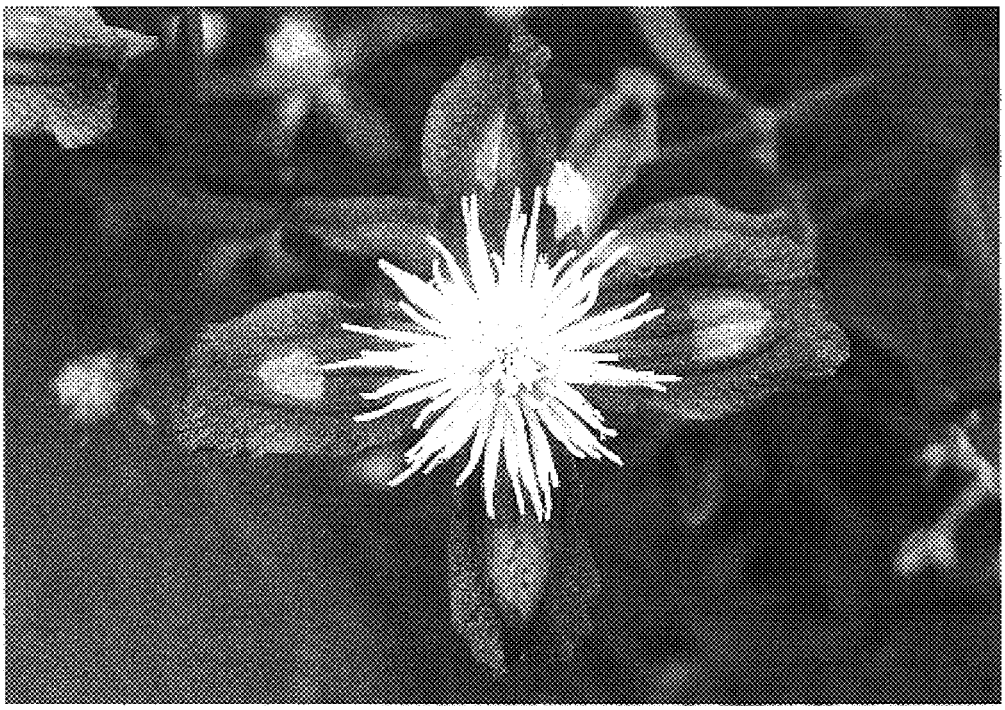
Figure 3:
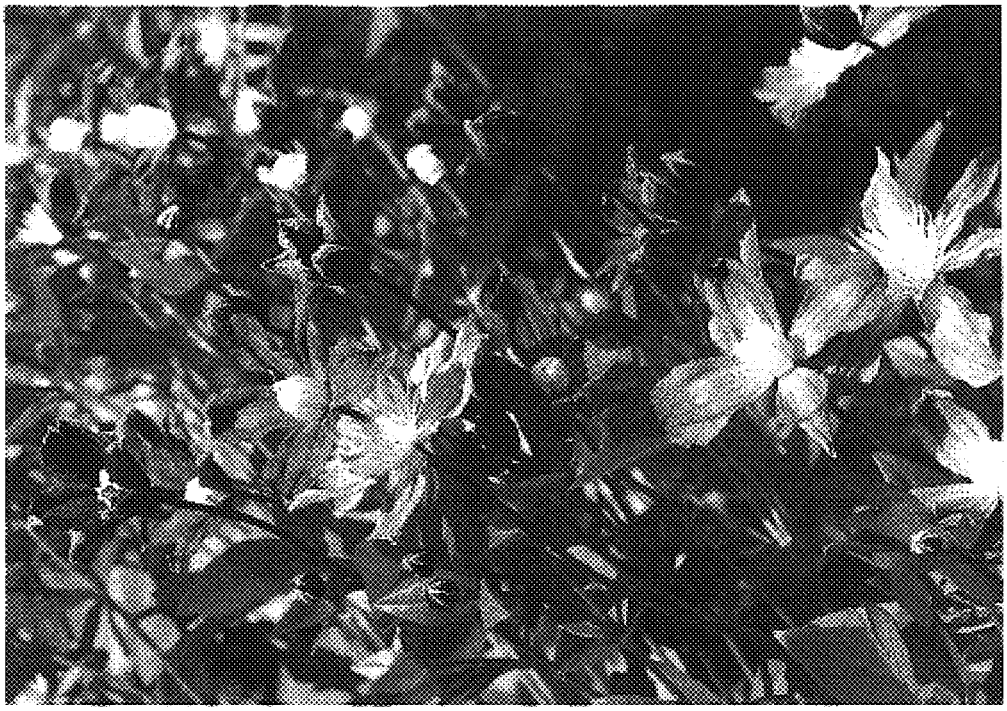

The photograph in FIG. 2 is a close-up view of a mature flower in early July and the photograph in FIG. 3 was taken in mid June and illustrates the progression of flower development.

The colors in the photographs are as close as possible with the digital photography techniques available, the color values cited in the detailed botanical description accurately describe the colors of the new *Clematis.*

DETAILED BOTANICAL DESCRIPTION

The following is a detailed description of the new cultivar as grown outdoors in full sun in a test plot in Mound, Minn. for three years. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Botanical classification.*—'Center Star' is an interspecific hybrid of *Clematis.*

*Common name.*—'Center Star' *Clematis.*

*Parentage.*—Hybrid derived from the female parent *Clematis integrifolia* (unnamed selection) and the male parent *Clematis hexapetala* (unnamed selection).

*Blooming period.*—Strong bloom for 4 to 6 weeks beginning mid to late June with scattered blooms for the remainder of the growing season in Minnesota.

*Plant habit.*—Herbaceous perennial, upright then decumbent.

*Height and spread.*—Three year-old plant is about 13 cm at base, height is about 100 cm in full bloom (stem height) if bound to remain upright.

*Cold hardiness.*—USDA Zone 3.

*Culture.*—Moist but well-drained soils in full sun to partial shade.

*Diseases and pests.*—No susceptibility or resistance to diseases or pests known to affect *Clematis* has been observed for 'Center Star'.

*Root description.*—Fibrous.

Growth and propagation:

*Propagation.*—Terminal stem cuttings from vegetative shoots.

*Root initiation.*—Roots develop in 6 weeks in summer under greenhouse conditions under intermittent mist without supplemental lighting.

*Time required for root development.*—75 to 90 days to develop a 2-inch container from a 6 to 8-inch cutting.

*Growth rate.*—Moderately vigorous once planted in the landscape.

Stem description:

*Shape.*—Round with ridges.

*Stem color.*—146A, ridges are tinted with 187A, 166A at base as the stems become woody.

*Stem size.*—About 100 cm (including peduncle and terminal pedicel) in length, average of 4 to 5 mm in diameter.

*Stem surface.*—Glabrous in appearance, fine hairs.

*Internode length.*—Average of 6 to 9 cm.

*Branching.*—Basal branches, typically two opposite peduncles branch from upper three nodes.

*Tendrils.*—Not present.

Foliage description:

*Leaf shape.*—Ovate.

*Leaf division.*—Simple, terminal leaves are deeply incised and leaflets-like.

*Leaf base.*—Aequilateral, rounded, clasping to stem.

*Leaf apex.*—Acute.

*Leaf fragrance.*—None.

*Leaf venation.*—Primary pattern tri-nerved, not prominent or conspicuous, same as leaf color.

*Leaf margins.*—Lower leaves are entire, upper leaves tripartite, terminal leaves typically tripartite with two additional opposite lower segments, 1 to 2 cm from upper segment.

*Leaf arrangement.*—Opposite.

*Leaf attachment.*—Sessile.

*Leaf surface.*—Glabrous, slightly pubescent on lower surface.

*Leaf size.*—Up to 10 cm in length, up to about 10 cm in length near base, on terminal leaves, tripartite portion averages 8 cm in length and 6 cm in width with the two lower segments about 6 to 7 cm in length and about 2.5 cm in width.

*Immature leaf color.*—Upper surface; between 137A and 147A, lower surface; 147B.

*Mature leaf color.*—Upper surface; 147A, lower surface; 147B.

*Peduncle size.*—8 to 10 cm in length, 2 mm in width, branches into two lateral branches up to 6 cm in length, 2 mm in width with two leafy bracts at base of pedicels.

*Peduncle color.*—146A tinted with 187A.

*Peduncle bracts.*—Ovate in shape, simple to trilobed, same as leaf colors, in opposite pairs, up to 6 cm in length and 3 cm in width, acute apex, rounded base, glabrous in texture.

*Peduncle surface.*—Glabrous with fine white hairs.

*Pedicel size.*—Up to 18 cm in length (average of 11 cm) on terminal flower and about 2 to 6 cm on lateral peduncles, 1 to 2 mm in width.

*Pedicel color.*—146A tinted with 187A.

*Pedicel surface.*—Glabrous with fine white hairs.

Inflorescence description:

*Inflorescence type.*—Dichasium cyme.

*Inflorescence arrangement.*—Typically arise from peduncles at upper 3 nodes plus one terminal flower.

*Bud description.*—Globose to ovoid in shape with acute apex, up to 2 cm in length and 1 cm in width when color appears, 79A in color with 5 to 7 grey vertical ridges (201C) 0.5 to 1 mm in width running length of bud, as bud opens inside surface 79A blushed with N88D.

*Flower fragrance.*—None.

*Lastingness of flowers.*—Individual flowers last about 10 days until tepals drop, stamens subsequently drop.

*Flower quantity.*—About 7 per peduncle, about 40 flowers per stem, about 400 on a three year-old plant.

*Flower type.*—Rotate, star-shaped, composed of 4 to 5 tepals.

*Flower aspect.*—Upward facing.

*Flower size.*—Typically 4 to 6.5 cm in diameter and 1.5 cm in depth.

*Tepal number.*—4 to 5.

*Tepal shape.*—Obelliptic.

*Tepal apex.*—Acute to rounded, often notched.

*Tepal base.*—Broadly cunneate.

*Tepal margins.*—Entire, wavy, with notches on apex.

*Tepal surface.*—Glabrous on upper surface, glabrous with pubescent edges on lower surface.

*Tepal color.*—Upper surface; when opening N88A, when mature N88A with center areas of 93B, 93C, 86 B and 155C (basically blue with violet and white markings), fades to 85D with shades of 91A. Lower surface; when opening N88A with pubescent edges N88C, when mature N88A with center areas of 93B, 93C, 86 B and 155C (basically blue with violet markings) and pubescent edges N88C, fades to 91A with lines of N89A. Center areas on both surfaces are composed blocks of color 5 mm in length and 8 mm in width with a white triangular block of white.

*Tepal size.*—2 to 3 cm length, 1 to 1.5 cm in width.

Reproductive organs:

*Gynoecium.*—Numerous pistils (about 100), style is silky in appearance, 1 cm in length, 0.6 cm in width and 155C in color, stigma is small and 13C in color, ovary is superior, 1C in color, 3 mm in height, 5 mm in width, broadly vase-shaped.

*Androcoecium.*—Numerous stamens (about 50 to 60), up to 1.5 cm in length, 0.5 mm in width, anther is 160C in color, no pollen present.

*Seed.*—'Center Star' is sterile, no seed heads are produced.

I claim:

1. A new and distinct cultivar of *Clematis* plant named 'Center Star' as herein illustrated and described.

* * * * *